United States Patent
Sheikhi et al.

(10) Patent No.: US 12,370,138 B2
(45) Date of Patent: Jul. 29, 2025

(54) BIOACTIVE GRANULAR HYDROGEL SCAFFOLDS AND USE THEREOF

(71) Applicant: The Penn State Research Foundation, University Park, PA (US)

(72) Inventors: Amir Sheikhi, University Park, PA (US); Arian Jaberi, University Park, PA (US); Mohammad Zaman Ataie, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 18/848,678

(22) PCT Filed: Mar. 29, 2023

(86) PCT No.: PCT/US2023/016658
§ 371 (c)(1),
(2) Date: Sep. 19, 2024

(87) PCT Pub. No.: WO2023/192343
PCT Pub. Date: Oct. 5, 2023

(65) Prior Publication Data
US 2025/0108006 A1      Apr. 3, 2025

Related U.S. Application Data

(60) Provisional application No. 63/424,286, filed on Nov. 10, 2022, provisional application No. 63/367,521, (Continued)

(51) Int. Cl.
*A61K 9/06* (2006.01)
*A61K 31/727* (2006.01)
(Continued)

(52) U.S. Cl.
CPC .............. *A61K 9/06* (2013.01); *A61K 31/727* (2013.01); *A61K 38/18* (2013.01);
(Continued)

(58) Field of Classification Search
CPC ........................................................ A61K 9/06
See application file for complete search history.

(56) References Cited

U.S. PATENT DOCUMENTS

2006/0040896 A1* 2/2006 Kennedy ................... A61P 7/02
514/56
2007/0280978 A1* 12/2007 Takada ..................... B82Y 5/00
424/618
(Continued)

FOREIGN PATENT DOCUMENTS

WO     WO-2020146031 A1 *  7/2020  ........... A61L 27/222

OTHER PUBLICATIONS

Gozde Basara, Xiaoshan Yue and Pinar Zorlutuna. "Dual Cross-linked Gelatin Methacryloyl Hydrogels for Photolithography and 3D Printing." Gels, vol. 5(34), 2019, pp. 1-14. (Year: 2019).*
(Continued)

*Primary Examiner* — Isaac Shomer
(74) *Attorney, Agent, or Firm* — Buchanan Ingersoll & Rooney PC

(57) ABSTRACT

Embodiments relate to a method of forming a granular hydrogel scaffold (GHS). The method comprises converting polymers to form hydrogel microparticles (HMP) via a first crosslinking and assembling the HMP to form GHS via non-light-mediated crosslinking with or without coating or embedding them with any biologies or nanoparticles.

12 Claims, 26 Drawing Sheets

Related U.S. Application Data filed on Jul. 1, 2022, provisional application No. 63/324,774, filed on Mar. 29, 2022.

(51) Int. Cl.
- *A61K 38/18* (2006.01)
- *A61K 38/30* (2006.01)

(52) U.S. Cl.
CPC ...... *A61K 38/1808* (2013.01); *A61K 38/1816* (2013.01); *A61K 38/1825* (2013.01); *A61K 38/1833* (2013.01); *A61K 38/1841* (2013.01); *A61K 38/185* (2013.01); *A61K 38/1858* (2013.01); *A61K 38/1866* (2013.01); *A61K 38/1875* (2013.01); *A61K 38/30* (2013.01)

(56) References Cited

U.S. PATENT DOCUMENTS

| | | | | |
|---|---|---|---|---|
| 2015/0031638 | A1* | 1/2015 | Ekre | A61P 7/00 514/25 |
| 2016/0279283 | A1* | 9/2016 | Griffin | A61L 26/0085 |
| 2020/0261616 | A1* | 8/2020 | Song | C08J 3/075 |
| 2021/0403649 | A1 | 12/2021 | Sheikhi et al. | |

OTHER PUBLICATIONS

Renato V. Iozzo and Liliana Schaefer. "Proteoglycan form and function: A comprehensive nomenclature of proteoglycans." Matrix Biology, vol. 42, 2015, pp. 11-55. (Year: 2015).*

Basara, G. et al., Dual crosslinked gelatin methacryloyl hydrogels for photolithography and 3D printing, Gels, Jul. 3, 2019 (Publication dated), vol. 5, Article No. 34, Internal pp. 1-14.

Seif-Naraghi, S. B. et al., Injectable extracellular matrix derived hydrogel provides a platform for enhanced retention and delivery of a heparin-binding growth factor, Acta Biomaterialia, Jun. 28, 2012 (Online publication date), vol. 8, pp. 3695-3703.

Trengove, A. et al., Microbial transglutaminase improves ex vivo adhesion of gelatin methacryloyl hydrogels to human cartilage, Frontiers in Medical Technology, Nov. 18, 2021 (Publication Date), vol. 3 Article No. 773673, Internal pp. 1-14.

Atunes, J. et al., In-air production of 3D co-culture tumor spheroid hydrogels for expedited drug screening, Acta Biomaterialia, Jun. 12, 2019 (Online publication date), vol. 94, pp. 392-409.

Atunes, J. et al., In-air production of 3D co-culture tumor spheroid hydrogels for expedited drug screening, Acta Biomaterialia, Jun. 12, 2019 (Online publication date), vol. 94, pp. 392-409, Supplementary Information.

International Search Report and Written Opinion for PCT/US2023/016658 filed Mar. 29, 2023 dated Jul. 17, 2023.

* cited by examiner

BIOACTIVE GRANULAR HYDROGEL SCAFFOLDS AND USE THEREOF

CROSS-REFERENCE TO RELATED APPLICATIONS

This patent application is the U.S. national stage application of International Patent Application No. PCT/US2023/016658, filed on Mar. 29, 2023, which is related to and claims the benefit of priority of U.S. provisional application Ser. No. 63/324,774, filed on Mar. 29, 2022, the entire contents of which is incorporated by reference, and is further related to and claims the benefit of priority of U.S. provisional application Ser. No. 63/367,521, filed on Jul. 1, 2022, the entire contents of which is incorporated by reference, and is further related to and claims the benefit of priority of U.S. provisional application 63/424,286, filed on Nov. 10, 2022, the entire contents of which is incorporated by reference.

STATEMENT REGARDING FEDERALLY SPONSORED RESEARCH DEVELOPMENT

This invention was made with government support under Grant No. NS121150 awarded by the National Institutes of Health. The Government has certain rights in the invention.

FIELD OF THE INVENTION

Embodiments relate to bioactive granular hydrogel scaffolds and methods of use and making thereof.

BACKGROUND OF THE INVENTION

Granular hydrogel scaffolds (GHS) have enabled rapid cell infiltration and downregulated inflammatory responses during tissue regeneration. Various polymers have been used as the building blocks of GHS, including hyaluronic acid (HA), polyethylene glycol (PEG), and gelatin methacryloyl (GelMA), via different crosslinking and assembly approaches. GelMA is methacryloyl-modified gelatin that can undergo physical (e.g., thermal) and chemical (e.g., free radical polymerization) crosslinking, providing a biocompatible network decorated with the cell-adhesive RGD motifs. Previously, GelMA has been used to form hydrogel microparticles (HMP) using microfluidic and other biofabrication techniques. GelMA HMP were physically crosslinked by lowering the temperature below the sol-gel temperature, followed by packing and UV light exposure to form covalent bonds among the HMP, converting them into GHS. The GelMA GHS has been used for tissue engineering and 3D bioprinting.

However, the physically crosslinked GelMA HMP dissolve at the physiological temperature (i.e., thermally unstable) and cannot form GHS. To overcome this material design challenge, individual HMP must be crosslinked via a chemical route that is orthogonal to HMP assembly/GHS formation.

BRIEF SUMMARY OF THE INVENTION

Embodiments relate to exemplary formulations and methods to convert protein/peptide-based materials and/or any other synthetic or semi-natural material, including carbohydrates and their derivatives, to granular hydrogel scaffolds that do not require light exposure for scaffold formation. A polymer can first be converted to stable microgels (microscale hydrogel particles) via chemical crosslinking (e.g., step 1), followed by microgel-microgel assembly using orthogonal, non-light-mediated crosslinking (e.g., step 2). Exemplary step 1 may involve a range of chemical crosslinking methods, such as free-radical polymerization of vinyl groups and any other technique. Exemplary step 2 may be based on the crosslinking of other functional groups that were not used in step 1, such as amines, using enzymes, dynamic covalent bond formation, or any other method.

Embodiments further relate to polymeric granular hydrogel scaffolds that may be formed inside of tissues that do not have access to light. Embodiments may provide additional, new opportunities for noninvasive or minimally invasive tissue regeneration using granular hydrogel scaffolds without requiring open surgery.

Embodiments further relate to microgels that may be decorated and/or encapsulated with other biological factors or nano-structure materials to further promote the biological function of granular hydrogels.

It is an object of the present disclosure to provide methods and formulations of converting polymers, such as proteins and/or peptides, to hydrogel microparticles that can form granular hydrogel scaffolds after injection in tissues.

It is a further object of the present disclosure to provide methods and formulations of crosslinking hydrogel microparticles in a way that they remain stable at the physiological temperature and undergo assembly after enzymatic activation to form granular hydrogel scaffolds.

It is a further object of the present disclosure to provide methods of crosslinking hydrogel microparticles such that they remain stable at the physiological temperature and undergo assembly after mixing with another polymer, such as aldehyde-modified hyaluronic acid, to form granular hydrogel scaffolds.

It is a further object of the present disclosure to provide methods and formulations of decorating hydrogel microparticles with biologics (e.g., growth factors, drugs, cells), followed by the hydrogel microparticle assembly to form granular hydrogel scaffolds with enhanced bioactivity (e.g., bioactive granular hydrogel scaffolds).

It is a further object of the present disclosure to provide methods and formulations of encapsulating biologics (e.g., growth factors, drugs, cells) in hydrogel microparticles, followed by hydrogel microparticle assembly to form bioactive granular hydrogel scaffolds.

It is a further object of the present disclosure to provide methods and formulations to form in situ granular hydrogel scaffold composites/nanocomposites that mimic the physicochemical and/or biological characteristics of native tissues, such as brain, skin, muscle, etc.

Conventional teachings related to embodiments described herein may be found in: U.S. Pat. No. 10,682,309, WO 2022/133429, AU 2020/088650, U.S. Pat. No. 10,117,967, and Daly, A. C.; Riley, L.; Segura, T.; Burdick, J. A. Hydrogel microparticles for biomedical applications. *Nat Rev Mater.* 2020.

In an exemplary embodiment, a method of forming a granular hydrogel scaffold comprises converting polymers to form hydrogel microparticles via a first crosslinking; and assembling the hydrogel microparticles to form the granular hydrogel scaffold via a second crosslinking, wherein the second crosslinking is a non-light-mediated crosslinking.

In some embodiments, the polymers are selected from the group consisting of proteins, peptides, carbohydrates, lipids, or any other natural, semi-natural, and/or synthetic material, including hyaluronic acid, polyethylene glycol, and gelatin methacryloyl.

In some embodiments, the first crosslinking comprises physical crosslinking and/or chemical crosslinking.

In some embodiments, the method further comprises injecting the hydrogel microparticles into a tissue prior to assembling the hydrogel microparticles.

In some embodiments, the method further comprises mixing the hydrogel microparticles with additional polymers and/or colloidal particles prior to assembling the hydrogel microparticles.

In some embodiments, the additional polymers are selected from the group consisting of aldehyde-modified carbohydrates and/or proteoglycans, including hyaluronic acid and protein and/or polymers in the extracellular matrix of a native tissue.

In some embodiments, the method further comprises decorating the hydrogel microparticles with biologics and/or colloidal particles and/or hybrid biologics-colloids prior to assembling the hydrogel microparticles.

In some embodiments, the hydrogel microparticles are coated with the biologics and/or colloidal particles and/or hybrid biologics-colloids.

In some embodiments, the biologics and/or colloidal particles and/or hybrid biologics-colloids are encapsulated in the hydrogel microparticles.

In some embodiments, the biologics and/or colloidal particles and/or hybrid biologics-colloids are loaded to, attached on the surface of, or hybridized with nanocarriers bearing crosslinkable functional groups.

In some embodiments, the biologics are selected from the group consisting of biomolecules, growth factors, cytokines, enzymatically modified DNA, drugs, and peptides. In some embodiments, the biologics are physically and/or chemically attached to colloids, including heparin nanoparticles.

In some embodiments, the growth factors are selected from the group consisting of hematopoietic growth factors, EGF, FGF, NGF, PDGF, VEGF, IGF, GMCSF, GCSF, TGF, Erythropieitn, TPO, BMP, HGF, GDF, Neurotrophins, MSF, SGF, GDF, or any other growth factors or any other biomacromolecules. In some embodiments, the growth factors are physically and/or chemically attached to colloids, including heparin nanoparticles.

In an exemplary embodiment, a method for regenerating tissue, inducing vascularization, inducing axonogenesis, and/or improving tissue function via a granular hydrogel scaffold comprises forming hydrogel microparticles from polymers via a first crosslinking; injecting the hydrogel microparticles at an injection site within the tissue; and assembling the hydrogel microparticles to form the granular hydrogel scaffold via a second crosslinking, wherein the second crosslinking is a non-light-mediated crosslinking, and wherein the injection site does not have access to light.

In some embodiments, the granular hydrogel scaffold is configured to mimic the physiochemical and/or biological characteristics of the tissue.

In some embodiments, the granular hydrogel scaffold is configured to mimic the stiffness of the tissue.

In some embodiments, the tissue is selected from the group consisting of soft and/or hard tissues, including nervous tissue (brain, spinal cord, nerves), epithelial tissue (skin, GI tract), muscle tissue (cardiac muscle, smooth muscle, skeletal muscle), and/or connective tissue (fat, bone, tendon, cartilage).

In some embodiments, the first crosslinking comprises physical crosslinking and/or chemical crosslinking.

Further features, aspects, objects, advantages, and possible applications of the present invention will become apparent from a study of the exemplary embodiments and examples described below, in combination with the Figures, and the appended claims.

BRIEF DESCRIPTION OF THE FIGURES

The above and other objects, aspects, features, advantages, and possible applications of the present invention will be more apparent from the following more particular description thereof, presented in conjunction with the following drawings. It should be understood that like reference numbers used in the drawings may identify like components.

DETAILED DESCRIPTION OF THE INVENTION

The following description is of an embodiment presently contemplated for carrying out the present invention. This description is not to be taken in a limiting sense but is made merely for the purpose of describing the general principles and features of the present invention. The scope of the present invention should be determined with reference to the claims.

Embodiments relate to a bioactive granular hydrogel scaffold (GHS). The GHS may be used for tissue engineering and three-dimensional (3D) bioprinting. In particular, the GHS do not require light exposure for scaffold formation and may be formed inside of tissues that do not have access to light. This is advantageous as it allows for noninvasive or minimally invasive tissue regeneration, vascularization inducement, axonogensis inducement, and/or tissue function improvement techniques using the GHS without requiring open surgery.

Figure 1:
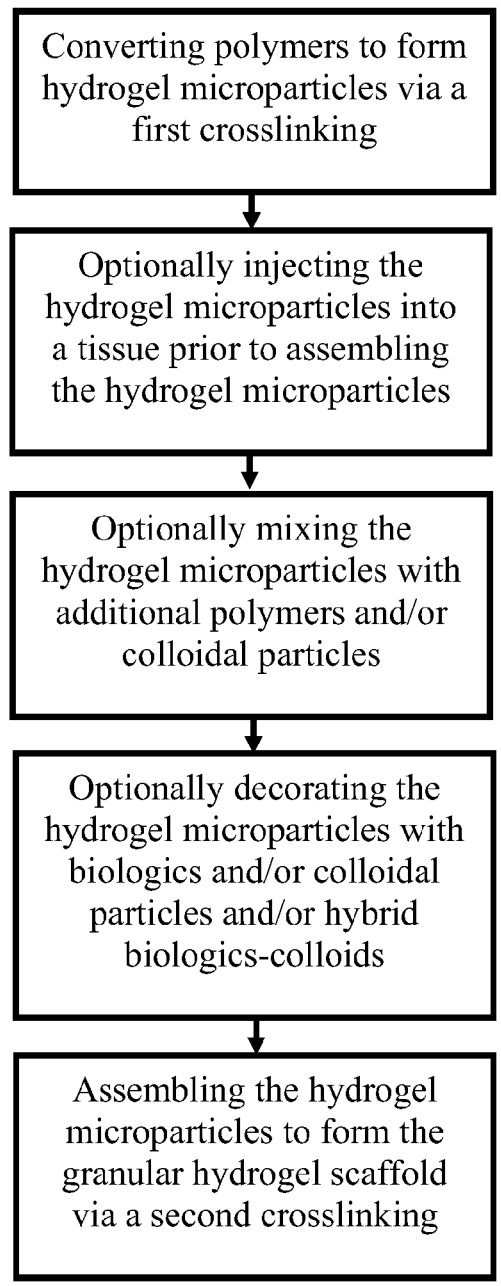
FIG. 1 shows an exemplary method for forming an embodiment of the granular hydrogel scaffolds.

Referring to FIG. 1, embodiments relate to a method of forming a granular hydrogel scaffold. The method comprises converting polymers to form hydrogel microparticles (HMP) via crosslinking and assembling the HMP to form GHS via non-light-mediated crosslinking.

In exemplary embodiments, the polymers may be any suitable polymers including protein-based materials and peptide-based materials. In particular, the polymers may be selected from the group consisting of any proteins, peptides, carbohydrates, lipids, or any other natural, semi-natural, and/or synthetic material. These can include hyaluronic acid (HA), polyethylene glycol (PEG), and gelatin methacryloyl (GelMA).

In exemplary embodiments, the polymers may be converted to form stable HMP. The polymers may be converted to the HMP via physical crosslinking and/or chemical crosslinking. Examples of chemical crosslinking include free radical polymerization (e.g., free radical polymerization of vinyl groups) or any other suitable chemical crosslinking techniques.

It is contemplated that HMP with any shape, size, and aspect ratio may be used. In a preferred embodiment, the shape of the HMP is spherical or rod-like. In a preferred embodiment, the size of the HMP is between 10-200 μm. In a preferred embodiment, the aspect ratio of the HMP is between 1-10.

It is contemplated that the terms "microgel" and "hydrogel microparticle" are used interchangeable throughout the present disclosure.

In exemplary embodiments, the HMP are injected to an injection site within tissue. It is contemplated that the HMP assemble to form the GHS after injection into the tissue via non-light-mediated crosslinking. It is contemplated that this step of crosslinking may be based on crosslinking of functional groups not used to crosslink the polymer to form the HMP, such as amines, using enzymes, dynamic covalent bond formation, or any other suitable crosslinking technique.

It is further contemplated that the HMP may assemble to form GHS after mixing with another polymer and/or colloidal particles. It is contemplated that this polymer may be aldehyde-modified carbohydrates and/or proteoglycans, including hyaluronic acid, protein and/or polymers in the extracellular matrix of native tissues, or another other suitable polymer that may form a hybridized GHS.

It is further contemplated that the HMP may assemble to form GHS after being decorated with biologics and/or colloidal particles and/or hybrid biologics-colloids. The surface of the HMP may be coated with any biologics and/or the biologics may be encapsulated in the HMP. The biologics may be biomolecules, growth factors (e.g., of hematopoietic growth factors, EGF, FGF, NGF, PDGF, VEGF, IGF, GMCSF, GCSF, TGF, Erythropieitn, TPO, BMP, HGF, GDF, Neurotrophins, MSF, SGF, and GDF and any other growth factors or biomacromolecules), cytokines, enzymatically modified DNA, drugs, peptides, or any combination thereof, or any other suitable biologics that may form GHS with enhanced bioactivity (e.g., a bioactive GHS). In exemplary embodiments, the biologics may be loaded (i.e., conjugated) to, attached on the surface of, or hybridized with nanocarriers bearing crosslinkable functional groups (e.g., vinyl groups). In exemplary embodiments, the biologics (e.g., the growth factors) are physically and/or chemically attached to colloids (e.g., heparin nanoparticles).

Figure 8:
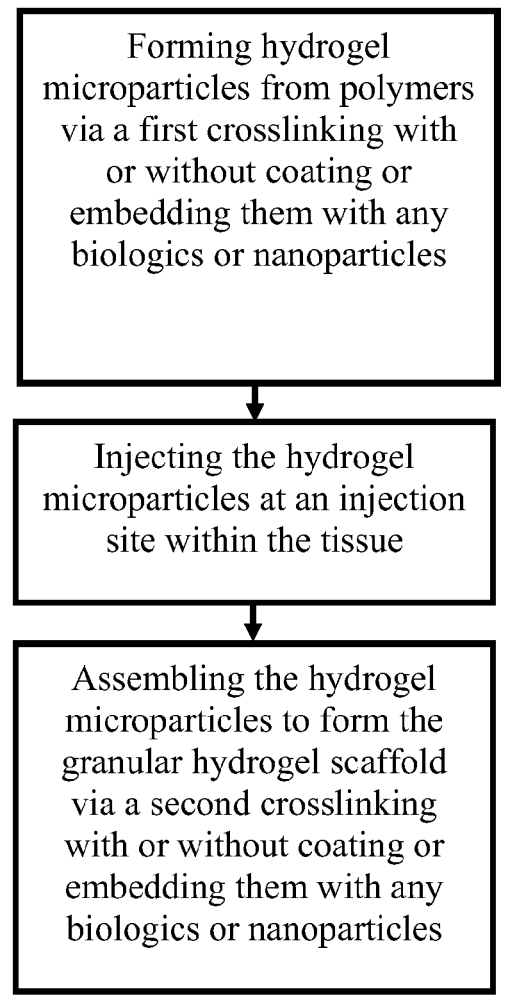
FIG. 8 shows an exemplary method for regenerating tissue via the granular hydrogel scaffold.

Referring to FIG. 8, embodiments relate to a method of regenerating tissue, inducing vascularization, inducing axonogenesis, and/or improving tissue function via a granular hydrogel scaffold. The method comprises forming HMP derived from polymers via crosslinking, injecting the HMP at an injection site within the tissue, and assembling the HMP to form the GHS via non-light-mediated crosslinking. It is contemplated that the GHS may be configured to mimic the physiochemical and/or biological characteristics of the tissue. In particular, the GHS may be configured to mimic the stiffness of the tissue.

In exemplary embodiments, the tissue is selected from the group consisting of soft and/or hard tissues, including nervous tissue (brain, spinal cord, nerves), epithelial tissue (skin, GI tract), muscle tissue (cardiac muscle, smooth muscle, skeletal muscle), and/or connective tissue (fat, bone, tendon, cartilage).

EXAMPLES

Materials

Gelatin type A (Sigma-Aldrich, USA), Dulbecco's phosphate buffered saline (DPBS) (Sigma-Aldrich, USA), methacrylic anhydride (Sigma-Aldrich, USA), and dialysis membranes (cutoff $M_w$=12-14 kDa, Spectrumlabs, USA) were used for GelMA synthesis. Lithium phenyl-2,4,6-trimethylbenzoylphosphinate (LAP) (Allevi, USA), (4-(2-hydrozyethyl)-1-piperazineethanesulfonic acid (HEPES) (Gibco, USA), Picosurf (Sphere Fluidics Inc, UK), Novec 7500 (3M, USA), and perfluorooctanol (PFO) (Sigma-Aldrich, USA) were used for GelMA HMP fabrication. $Ca^{2+}$ (Thermo scientific, USA), thrombin (EMD Millipore, USA), and Factor XIII (FXIII) (EMD Millipore, USA) were used for the assembly of GelMA HMP to form GHS. Fluorescein isothiocyanate (FITC) (Sigma-Aldrich, USA) was used for labeling the void spaces of GelMA GHS.

GelMA Synthesis

GelMA has been synthesized in the following manner. Briefly, 10% w/v gelatin type A was dissolved in 50° C. DPBS and reacted with methacrylic anhydride 1.25% (v/v) for 2 h. The reaction was stopped by adding DPBS (twice the reaction volume). The GelMA solution was dialyzed against 40° C. miliQ water using dialysis membranes (cutoff $M_w$=12-14 kDa) for 7 days. The GelMA solution was then filtered and frozen for 3 days at −80° C., followed by freeze-drying at 0.12 mbar. The lyophilized GelMA was stored at 2-8° C. until further use.

GelMA Stiffness Optimization

Lyophilized GelMA was dissolved in the HEPES buffer (25 mM, pH=7.2-7.4) containing LAP (0.1% w/v). The final concentration of GelMA solution was 1, 1.5, 2, or 3% w/v. The GelMA solutions were transferred to a mold and stored at 2° C. overnight to physically crosslink, followed by UV light (wavelength=395 nm) exposure at an intensity of 15 mW cm$^{-2}$ for 30 or 60 s. The photocrosslinked GelMA was punched with an 8 mm biopsy puncher and transferred to a rheometer (TA instrument, USA) to perform frequency sweep tests at a strain rate of 0.1% and angular frequencies of 0.1 to 100 rad s$^{-1}$. As a proof-of-concept, the average value of photocrosslinked GelMA storage modulus (G') at 1 rad s$^{-1}$ was assessed to optimize the GelMA stiffness/concentration for brain studies. This disclosure is valid for any concentration of GelMA or any other protein/peptide/biopolymer.

GelMA HMP Fabrication and Stabilization

The GelMA droplet formation may be conducted using a step emulsification or any other device or bulk emulsification. Briefly, a GelMA solution at the optimum polymer concentration that would yield the target tissue stiffness after crosslinking (e.g., 1.5% w/v to mimic brain) was dissolved in the HEPES buffer containing LAP (0.1% w/v). To form GelMA droplets in an oil phase, the GelMA solution was flowed into a microfluidic device as a dispersed aqueous phase, and an oil containing Picosurf 2% (v/v) in Novec 7500 was used as the continuous phase. The GelMA droplets were stored at 2-4° C. to undergo physical crosslinking.

After collecting the GelMA droplets, the emulsion was broken using a PFO solution in Novec 7500 oil (20% w/w). In addition, the microgels were mixed and centrifuged with the solution of 0.1% (w/v) LAP in HEPES to completely remove the oil. The washed microgels were spun down and suspended in a solution of 0.1% (w/v) LAP in HEPES at a concentration of 10% (v/v). Before photocrosslinking, the microgels were always maintained at 4° C. The diluted microgels were placed on a stirrer, and vigorously stirred while being exposed to the UV light (wavelength=395 nm, GearLight, USA) for 60 s at an intensity of 15 mW/cm$^2$. The UV exposure initiates the vinyl group-enabled covalent bond formation of GelMA. In this process, other types of crosslinkers, such as other photoinitiators and/or chemical agents (dithiothreitol, DTT) may also be used to stabilize the individual microgels. If the microgels are not stabilized, they immediately dissolve at 37° C. As the GelMA bears vinyl groups, thiol-based crosslinkers, such as DTT, can enable microgel stabilization via the Michael-type reaction between the vinyl and thiol groups. The GelMA within the individual HMP can also be crosslinked using click chemistry by modifying the GelMA carboxyl groups with pendant norbornene and tetrazine. Finally, the crosslinked microgels were stored in HEPES containing 10 mM of Ca$^{2+}$. To assess the stability of microgels, they were transferred to an incubator and imaged over time at 37° C. At timepoints of 0, 0.5, 1, 3, and 24 h, the microgels were imaged using a brightfield microscope. The microgel diameter was analyzed using a custom-written MATLAB code identifying the HMP border. Thermally stable microgels did not undergo significant size change over time.

GelMA HMP Modification

To enhance the bioactivity of GHS, embodiments enable the direct modification of GelMA HMP with biomolecules, growth factors (such as VEGF, SGF, and BMP), cytokines, enzymatically modified DNA, drugs, and/or peptides. These modifications can be conducted via GelMA HMP surface modification or encapsulation. In addition, the biologics, such as VEGF, can be loaded/conjugated to nanocarriers, such as heparin nanoparticles (nanoheparin, nH) bearing crosslinkable functional groups, such as vinyl groups. In this case, the growth factor-loaded nH can be directly conjugated to the surface of GelMA HMP through chemical (e.g., covalent) bond formation. The GelMA HMP surface may be coated with any biologics and/or the biologics may be encapsulated in the GelMA HMP. The modified HMP will remain annealable and form composite/nanocomposite GHS, similar to the unmodified HMP.

GelMA GHS Formation

The individually crosslinked GelMA HMP were incubated in the HEPES buffer containing 10 mM of Ca$^{2+}$ at room temperature, followed by packing at 14,000 rpm for 5 min. After centrifugation, the supernatant was removed and the excess water among the microgels was removed using a Kimwipe. The packed microgels were aliquoted to microcentrifuge tubes, each of which containing 88 μL of packed GelMA HMP. A solution of thrombin with a concentration of 2 U/mL in HEPES containing Ca$^{2-}$ (10 mM) and a solution of FXIII with a concentration of 10 U/mL in HEPES containing Ca$^{2+}$ (10 mM) were added to two separate aliquoted HMP tubes. Each GelMA HMP aliquot was well mixed with their respective biomacromolecule solutions (FXIII or thrombin), followed by pulse centrifugation. Then, the microgel assembly (GHS formation) was initiated by mixing an equal volume of thrombin-containing microgels and FXIII-containing microgels. Upon mixing, thrombin and calcium activate FXIII, yielding FXIIIa. The two microgel suspensions were mixed using a positive displacement pipette (Gilson, USA). The mixture was spun down at 14,000 rpm, and the supernatant was removed. The mixed microgel was transferred to a mold using a positive displacement pipet and incubated at 37° C. to initiate the FXIIIa-mediated formation of glutamyl-lysine bonds among HMP. In this system, the lysine and glutamine peptides were used to form the glutamyl-lysine bonds with the enzymatic reaction. In addition, based on the target tissue and application, other types of crosslinkers, such as glutaraldehyde, can perform a Schiff-base reaction between lysine and aldehyde groups. GelMA GHS may also be hybridized with other polymers, such as those in the extracellular matrix (ECM) of native tissues. As an example, polysaccharides such as hyaluronic acid (HA) or alginate, were modified with the aldehyde groups to form a Schiff base with protein HMP, such as GelMA. This is an important aspect of the disclosed subject matter, eliminating the necessity of using enzymes, such as thrombin or FXIII, which are expensive, easy to degrade, and often bioactive. Such mechanism can be generalized to other peptides and crosslinkers.

GelMA GHS Pore Characterization

To analyze the interconnected void spaces of GelMA GHS, the assembled scaffolds were assessed after 90 min of enzymatic assembly at 37° C. They were incubated with a FITC (Mw=0.5 MDa) solution (15 mM) for 5 min. The labelled scaffold was imaged using a fluorescence microscope (Leica DMI8, Germany). For each sample (at least 3 per condition), the z-stack images were acquired to analyze at least 3 layers of packed microgels within the scaffold. To analyze the scaffold porosity, the void fraction was calculated by adjusting the threshold of images using the Leica LAS X software. In addition, the median pore diameter of scaffolds was calculated by analyzing the equivalent area of individual pores using a custom-written MATLAB code (MATLAB 2021, USA).

Mechanical Characterization of GelMA GHS

The assembled GHS (height~1 mm) after 90 min of incubation at 37° C. were incubated in room temperature HEPES for 1 h. The scaffolds were punched with 8 mm biopsy puncher, placed on the Instron 5943 (Norwood, MA, USA) lower plate, and underwent compression while the force was measured using a 10 N load cell. The force-displacement data were converted to stress-strain curves. The compression tests were performed at a displacement rate of 1 mm min$^{-1}$. The compressive modulus of GHS was calculated based on the linear stress-strain region at strain ~0.05-0.15 mm mm$^{-1}$. At least 5 scaffolds per condition were analyzed for mechanical characterizations.

Statistical Analysis

The one-way analysis of variance (ANOVA) was performed for statistical analysis, and statistically significant differences were identified when p-values were lower than 0.05 (*p<0.05), 0.01 (p<0.01), 0.001 (*p<0.001), and 0.0001 (****p<0.0001).

Results and Discussion

GelMA GHS Formation

Figure 2A:
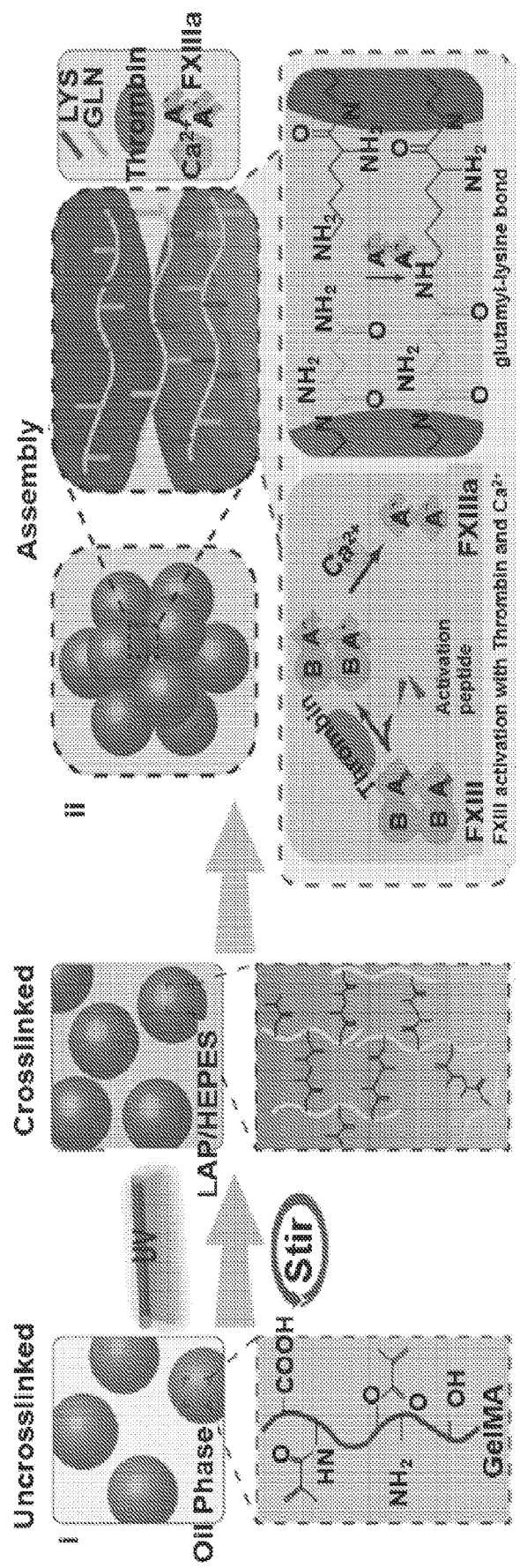
FIG. 2A shows a schematic of individual gelatin methacryloyl hydrogel microparticle photocrosslinking and the mechanism of hydrogel microparticle assembly via activated factor XIII-mediated glutamyl-lysine bond formation.

A multi-step procedure to first chemically stabilize HMP and then assemble them to form GHS is provided. GelMA HMP are first physically crosslinked at 2-4° C., followed by UV light (e.g., wavelength~395 nm and intensity~15 mW cm$^{-2}$ for 60 s) exposure in a dilute suspension of HEPES, containing LAP (0.1%, w/v) at 4° C. Throughout the UV exposure process, GelMA precursor within each HMP is chemically crosslinked via free radical polymerization, as schematically shown in FIG. 2A. GelMA contains various peptides, such as lysine (Lys) and glutamine (Gln). The biocompatible assembly of UV crosslinked GelMA HMP to form GelMA GHS is conducted via the enzymatic formation of glutamyl-lysine bonds. FXIII, also known as fibrin stabilizing factor, is a zymogen (an inactive material that is converted to an enzyme upon activation) found in human blood. Thrombin can activate FXIII to form activated FXIII (FXIIIa), which is an enzyme responsible for the crosslinking of fibrin during the blood coagulation cascade. FXIIIa catalyzes the formation of ε-(γ-glutamyl) lysine isopeptide bonds between the ε-amino groups of Lys residues (K peptide, donor) and γ-carboxamide groups of Gln residues (Q peptide, acceptor) of gelatin, similar to those of fibrin monomers.

FIG. 2A schematically presents the mechanism of GelMA GHS formation via the FXIIIa mediated glutamyl-lysine bond formation among the individual HMP. Accordingly, the GelMA HMP undergoes microgel-microgel assembly, catalyzed by the FXIIIa at 37° C., forming GelMA GHS.

Figure 2B:
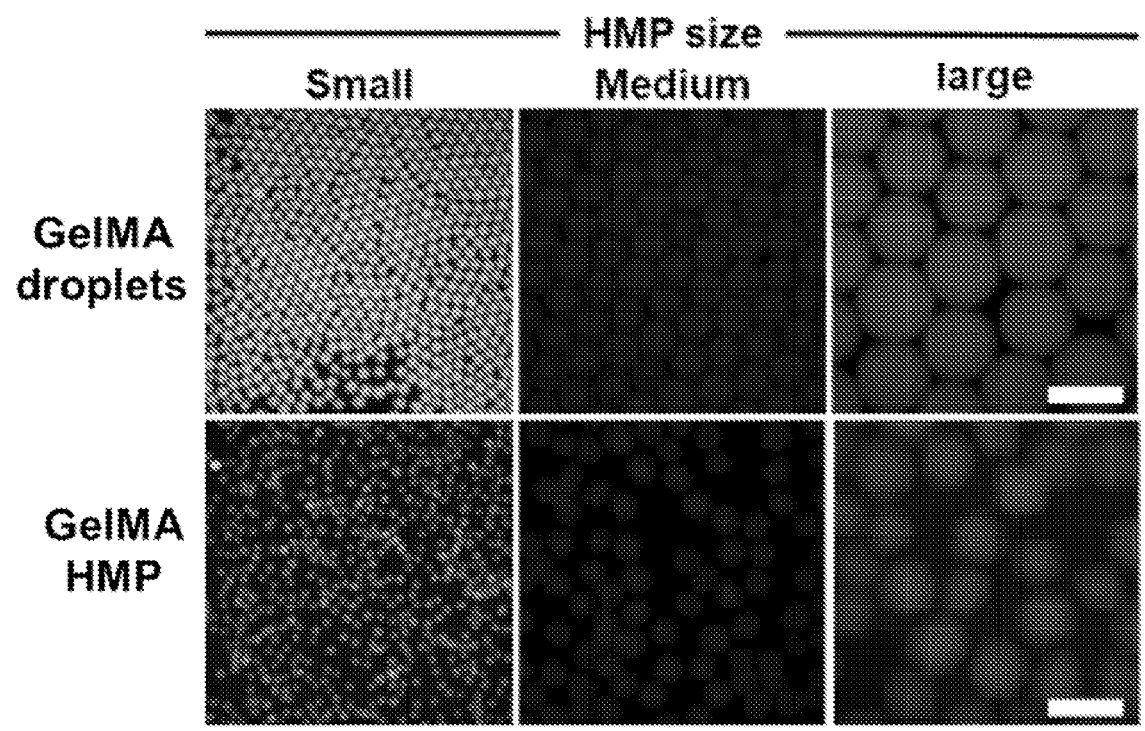
FIG. 2B shows gelatin methacryloyl droplets and hydrogel microparticles (photocrosslinked droplets), prepared in three sizes: small, medium, or large (scale bar is 200 µm).
Figure 2C:
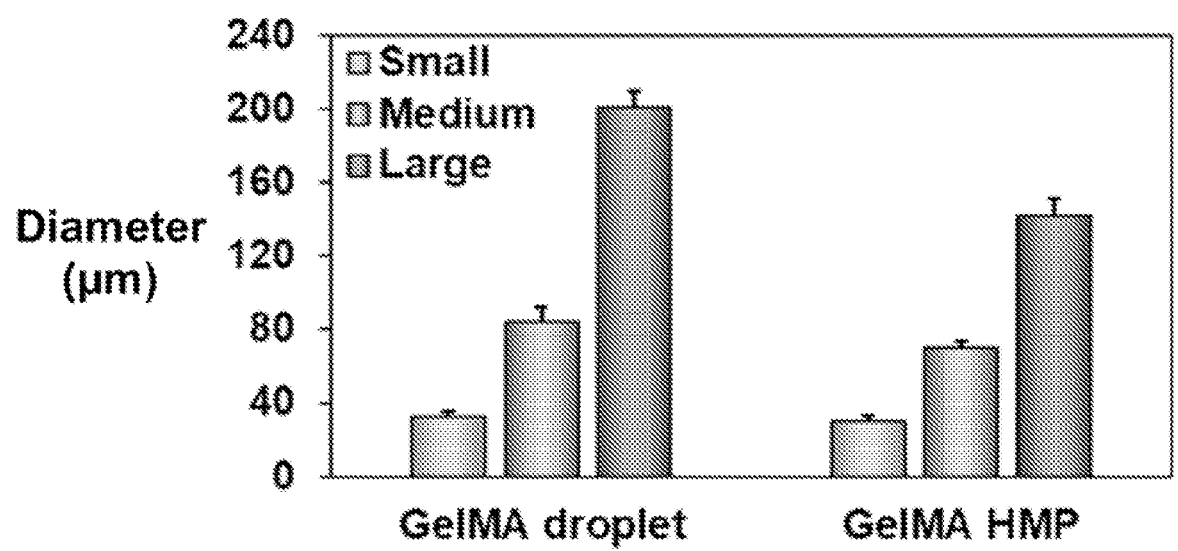
FIG. 2C shows the average diameter of gelatin methacryloyl droplets and hydrogel microparticles.

The pore characteristics of GHS directly regulate the scaffold-cell interactions, cell recruitment, foreign body response, and tissue regeneration. Accordingly, it is important to tailor the void space within GHS. The pore features of GHS are tuned by varying the size of HMP building blocks, as the pore size is regulated by the void space among the microgels. To engineer the pore size of GHS, various GelMA HMPs were fabricated with an average diameter of 31.9±3.2, 85.5±6.0, or 164.8±14.6 µm, labeled as small, medium, or large, respectively (see FIGS. 2B and 2C).

Figure 3A:
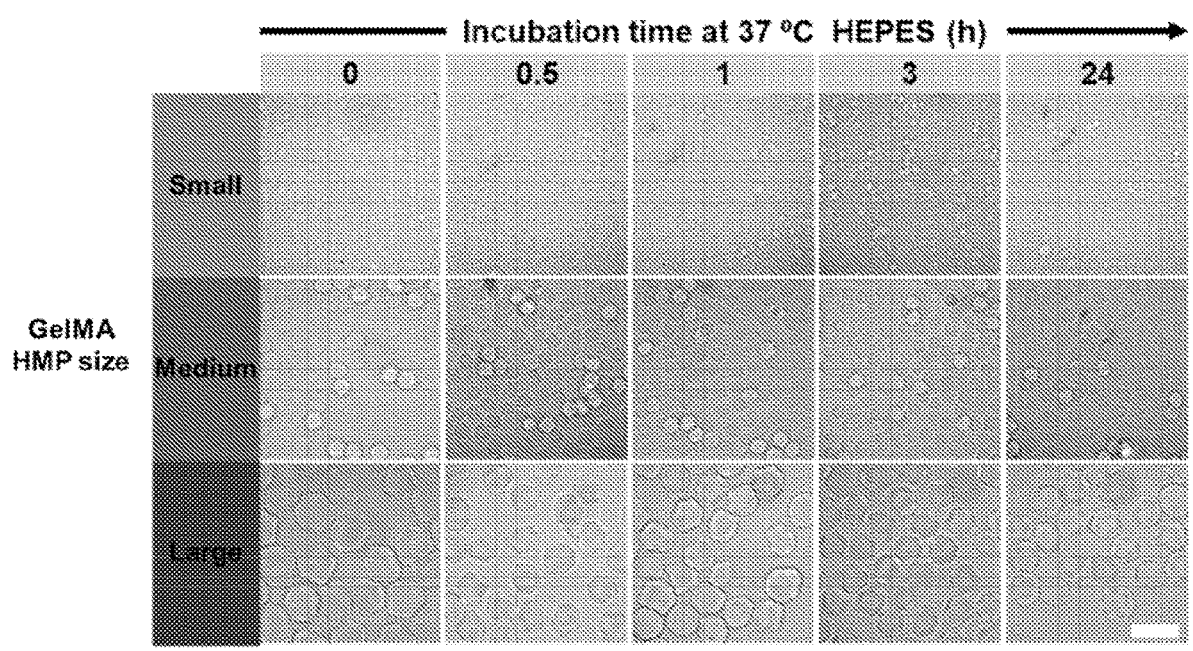
FIG. 3A shows optical images of small, medium, or large photocrosslinked gelatin methacryloyl hydrogel microparticles with gelatin methacryloyl concentration of 1.5% (w/v) and 60 s of UV exposure at the intensity of 15 mW cm$^{-2}$ incubated at 37° C. for up to 24 h (scale bar is 200 µm).
Figure 3B:
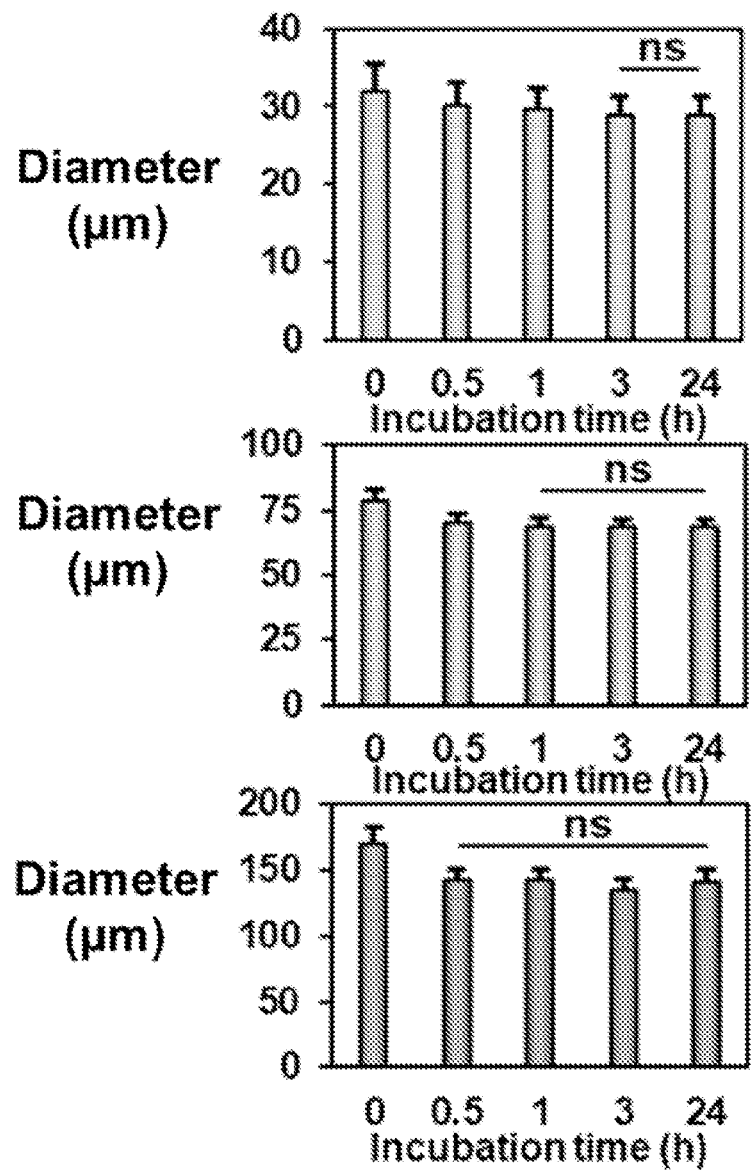
FIG. 3B shows diameters of hydrogel microparticles.

FIGS. 3A and 3B shows the size change of photocrosslinked GelMA HMP at 37° C. As can be seen in this figure, the photocrosslinked GelMA HMP are stable at the physiological temperature (before assembly). Finally, the GelMA GHS were fabricated by mixing the GelMA HMP with the FXIIIa, followed by packing and incubation at 37° C. for 90 min.

Figure 2D:
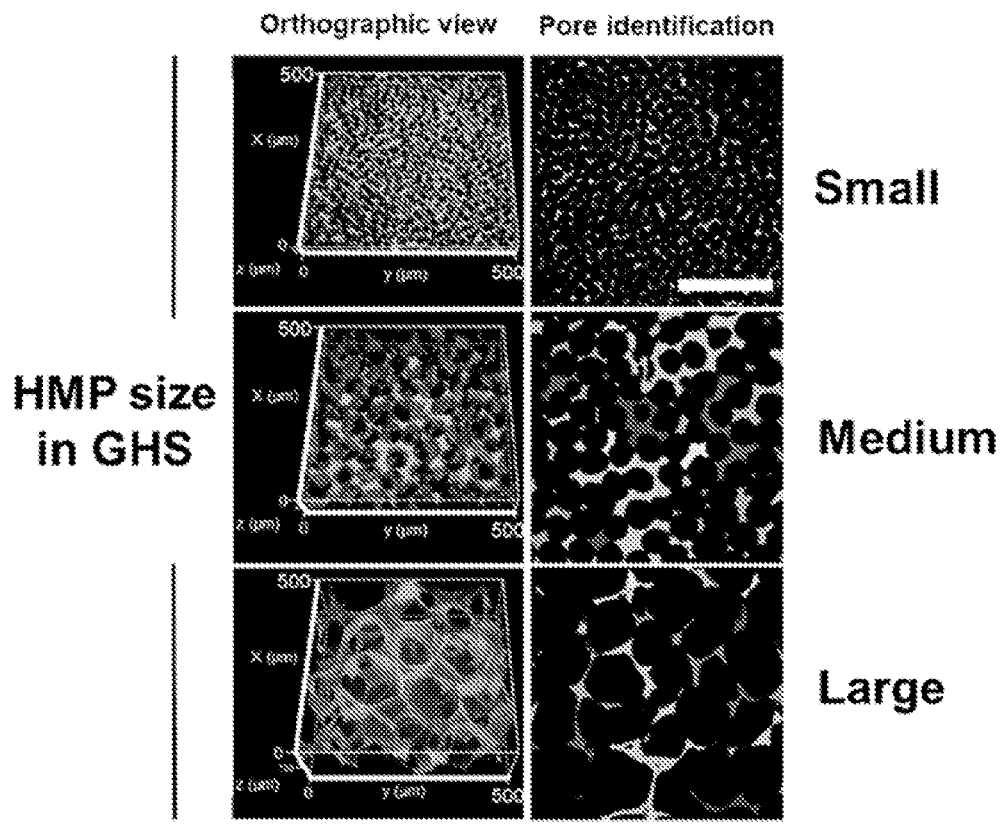
FIG. 2D shows the orthographic view and pore identification of gelatin methacryloyl granular hydrogel scaffolds, fabricated using small, medium, or large hydrogel microparticles (scale bar is 200 µm).

To demonstrate the interconnectivity of pores and analyze the pore features of GelMA GHS, the scaffolds were incubated with the FITC-dextran fluorescent dye. FIG. 2D shows the fluorescently labeled GelMA GHS, fabricated from three groups of GelMA HMP (small, medium, and large) as well as the identified pores using a custom-written MATLAB code.

Figure 2E:
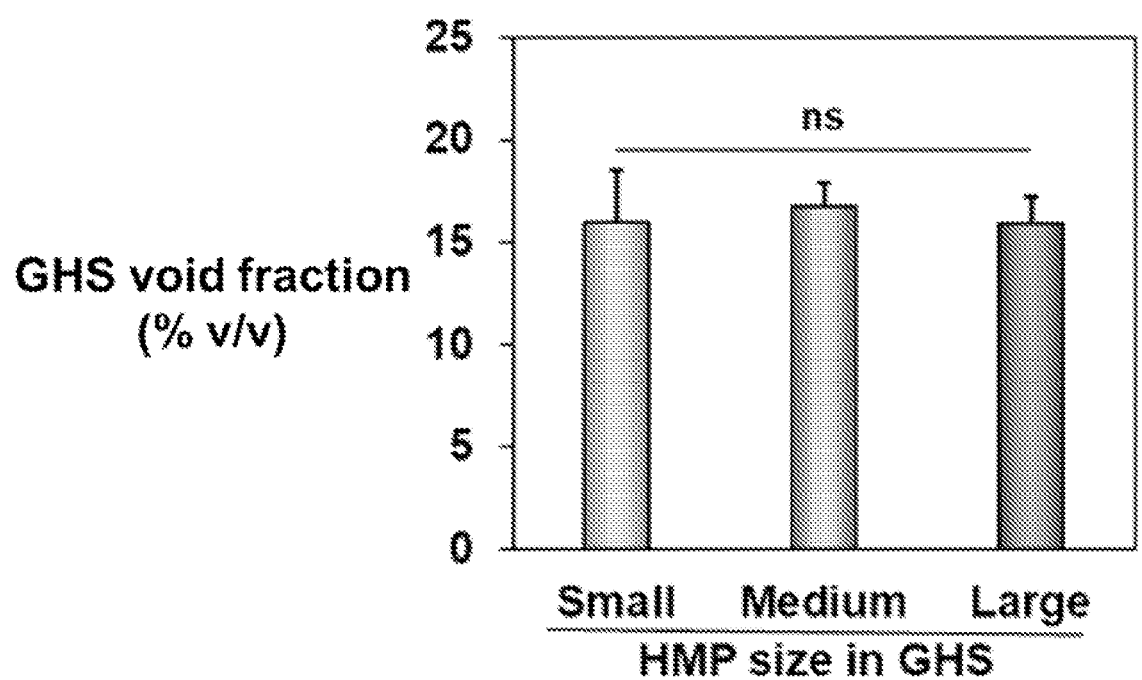
FIG. 2E shows gelatin methacryloyl granular hydrogel scaffolds void fraction.
Figure 2F:
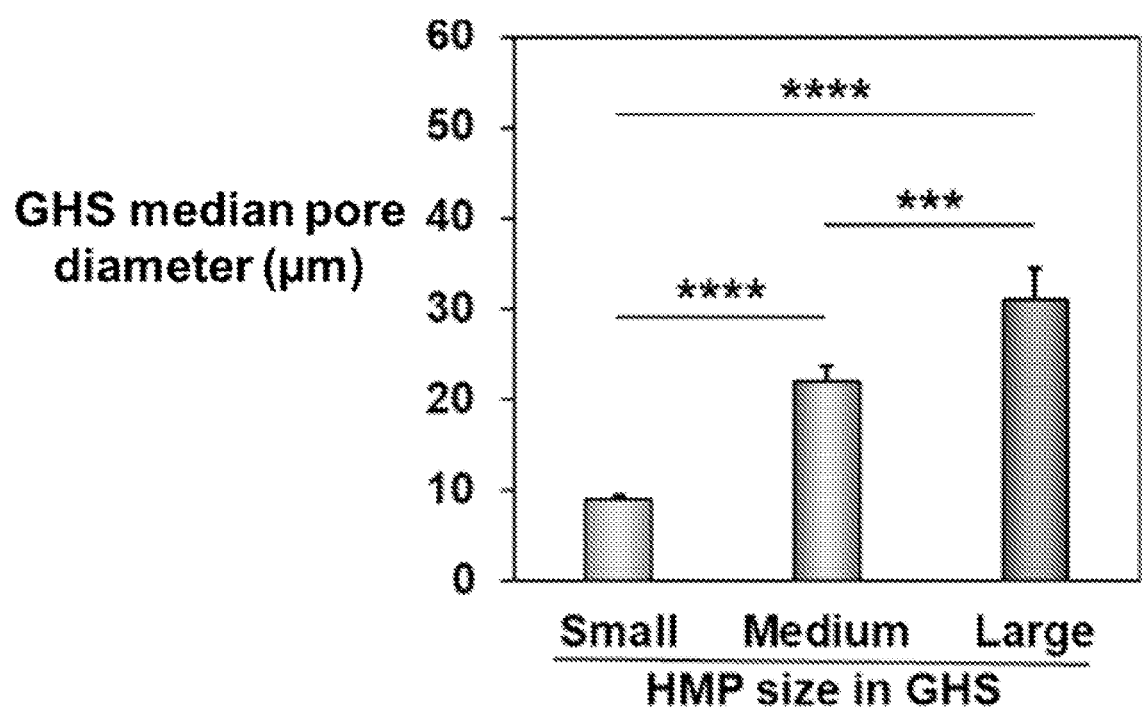
FIG. 2F shows equivalent median pore diameter of gelatin methacryloyl granular hydrogel scaffolds.

FIG. 2E shows the analysis of GelMA GHS void fraction, which suggests that the void fraction is independent of microgel size, and the average void fraction is ~16.0±2.4% (v/v). In addition, the median pore size of GelMA GHS was measured at a z-stack wherein the microgels have the largest contact with each other. The images were analyzed using the MATLAB code to detect the area of individual pores and calculate the equivalent pore diameter. As presented in FIG. 2E, the median pore diameter of GelMA GHS fabricated from the small, medium, and large HMP is ~8.9±0.4, 21.9±1.6, and 30.9±3.5 µm, respectively. These results show that although the void fraction is similar in all three groups of GHS as a result of spherical granules, the pore size significantly increases by increasing the microgel size.

Figure 2G:
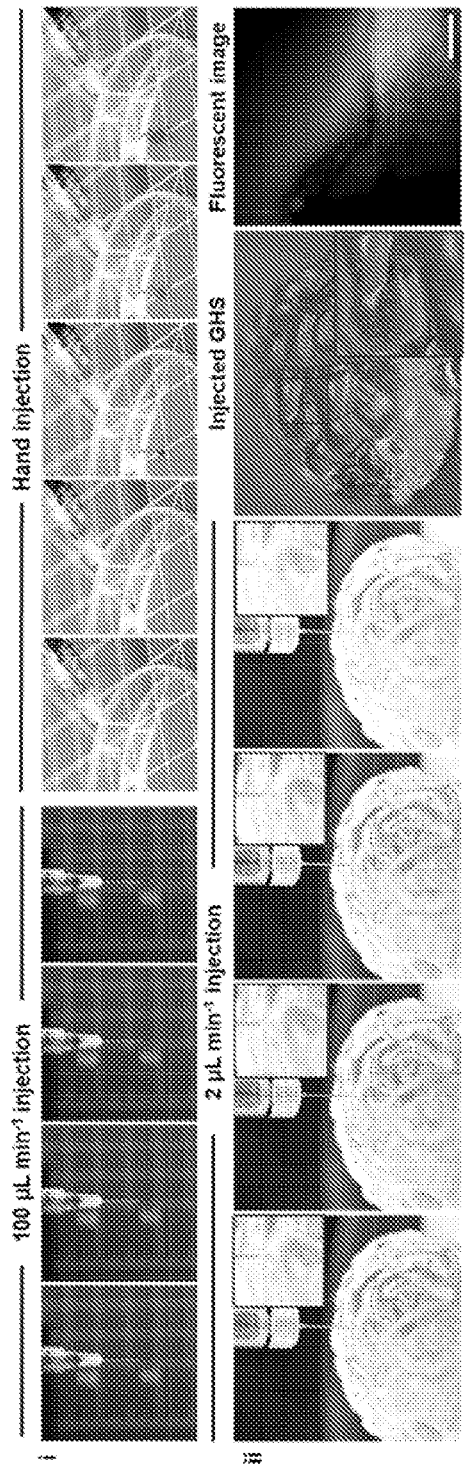
FIG. 2G shows injectability of packed gelatin methacryloyl hydrogel microparticles (scale bar is 200 µm).

FIG. 2G shows the injectability of packed GelMA HMP through 30G needles using a syringe pump or by hand, mimicking the brain injection process to facilitate tissue regeneration after stroke. FIG. 2G also presents the HMP injection via a 30G needle (Small Hub RN Needle, Hamilton, USA) connected to a 5 µL syringe (Hamilton, USA) using a syringe pump at a rate of 2 µL min$^{-1}$. As can be seen in FIG. 2G, the GelMA HMP is injectable via the clinically relevant needles, enabling scaffold formation in a lesion after injection.

Mechanical Characterization of GelMA HMP and GHS

Figure 4A:
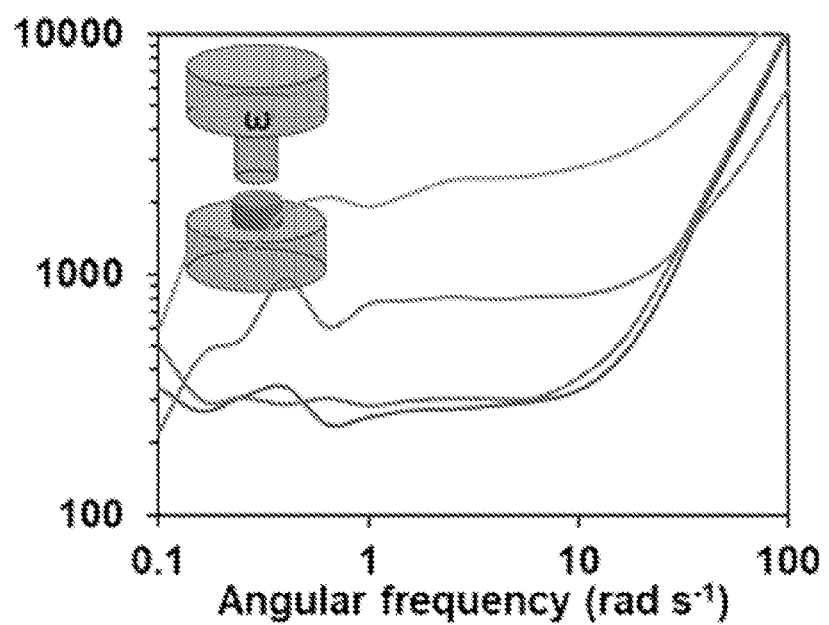
FIG. 4A shows frequency sweep tests to measure the storage modulus of bulk gelatin methacryloyl hydrogel (concentration=1, 1.5, 2, or 3% w/v in 4-(2-hydroxyethyl)-1-piperazineethanesulfonic acid, resembling hydrogel microparticles), photocrosslinked via UV light exposure for 30 s.
Figure 4B:
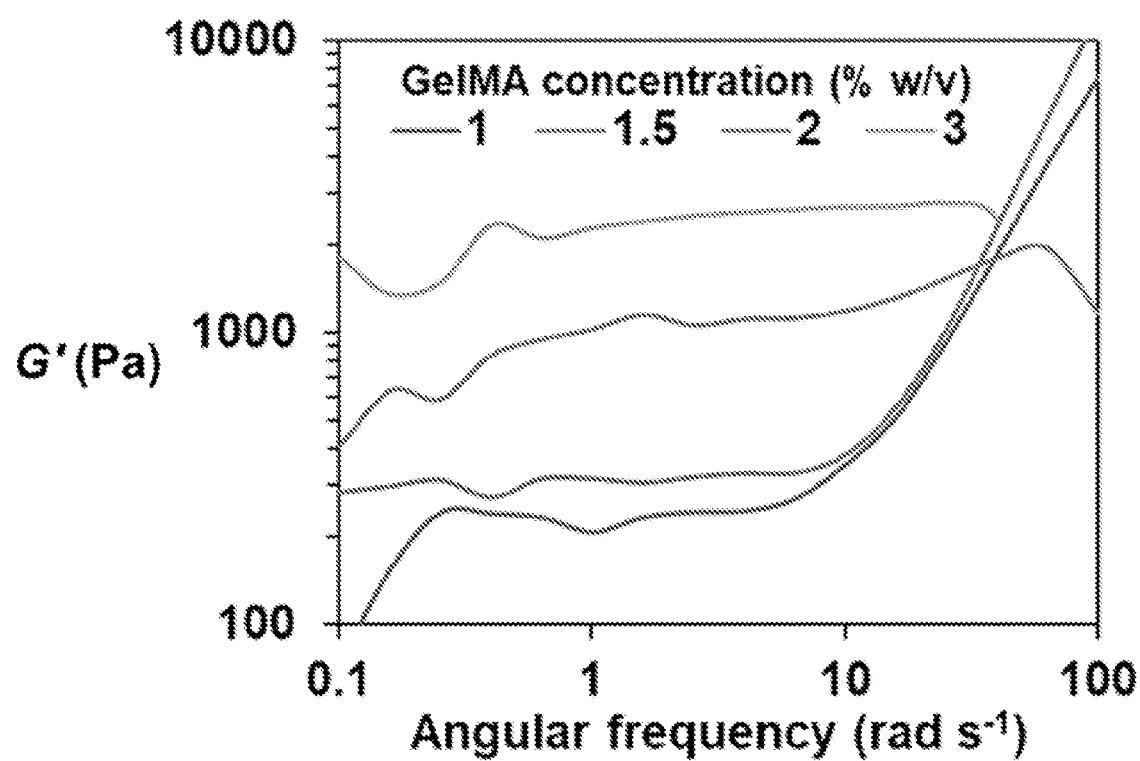
FIG. 4B shows frequency sweep tests to measure the storage modulus of bulk gelatin methacryloyl hydrogel (concentration=1, 1.5, 2, or 3% w/v in 4-(2-hydroxyethyl)-1-piperazineethanesulfonic acid, resembling hydrogel microparticles), photocrosslinked via UV light exposure for 60 s.

The mechanical properties of GelMA should be optimized to mimic target tissues. As an example, to match the stiffness of brain tissue, the stiffness of GelMA was tailored via changing the GelMA concentration and photocrosslinking time. Varying GelMA concentrations (1, 1.5, 2, or 3% w/v in HEPES, containing 0.1% LAP) were used to prepare physically crosslinked bulk samples maintained at 2-4° C. overnight, followed by UV light exposure for 30 s or 60 s at an intensity of 15 mW cm$^{-2}$. The representative storage modulus graphs are shown in FIGS. 4A and 4B for these exposure times, respectively.

Figure 4C:
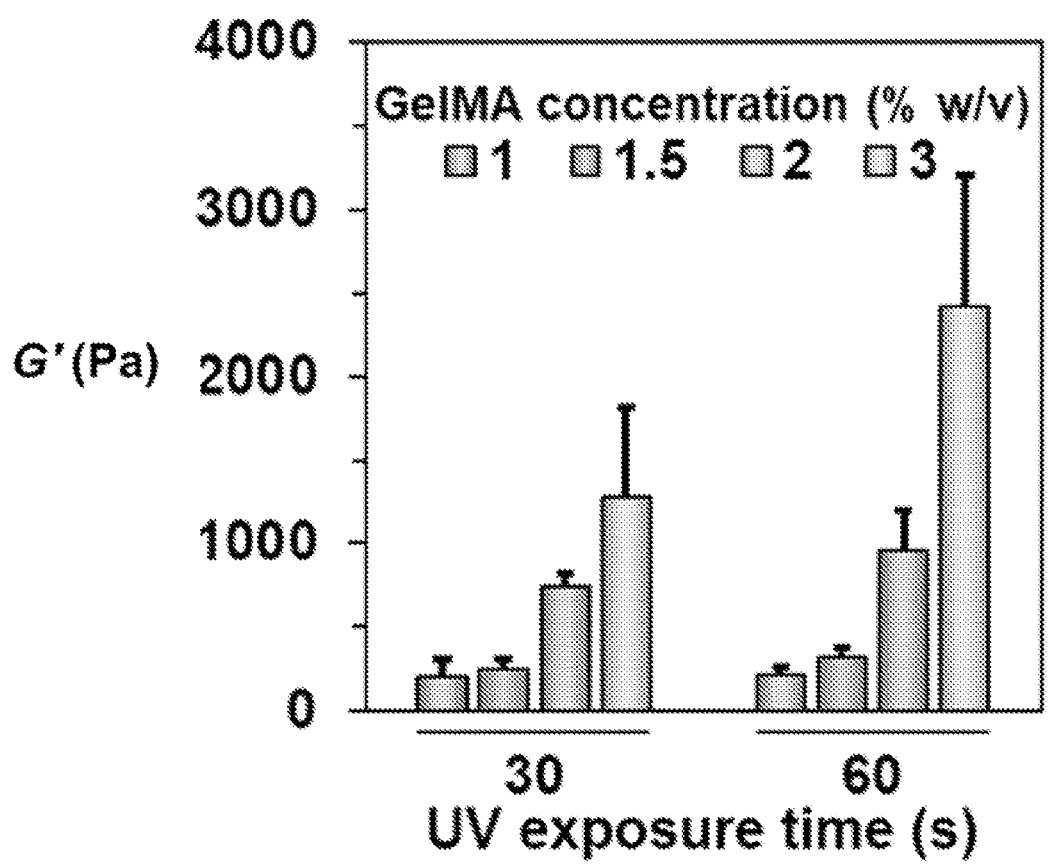
FIG. 4C shows the storage modulus of bulk gelatin methacryloyl scaffolds at a frequency of 1 rad s$^{-1}$ and oscillatory strain of 0.1%. The data represents mean±standard deviation for at least 3 samples.

FIG. 4C presents the average and standard deviation of bulk GelMA storage modulus at varying GelMA concentration and photocrosslinking times. The higher the biopolymer concentration or UV exposure time, the higher the storage modulus within the experimental range. The target average value of storage modulus at a frequency of 1 rad s$^{-1}$ is the native rat brain modulus of ~330 Pa. The average storage modulus of the GelMA with a concentration of 1.5% (w/v) and the UV curing time of 60 s was around 325 Pa, which has a good agreement with the native brain tissue (FIG. 4C). Note that the stiffness of the bulk samples represents the stiffness of individual GelMA HMP.

The HMP assembly process was initiated by mixing the GelMA HMP with FXIIIa, followed by incubation at 37° C.

To determine the stiffness of GelMA GHS, compression tests were performed on the GHS. The concentration of the FXIIIa was optimized based on the compressive modulus of assembled scaffolds, compared with packed unassembled ones (the control group).

Figure 4D:
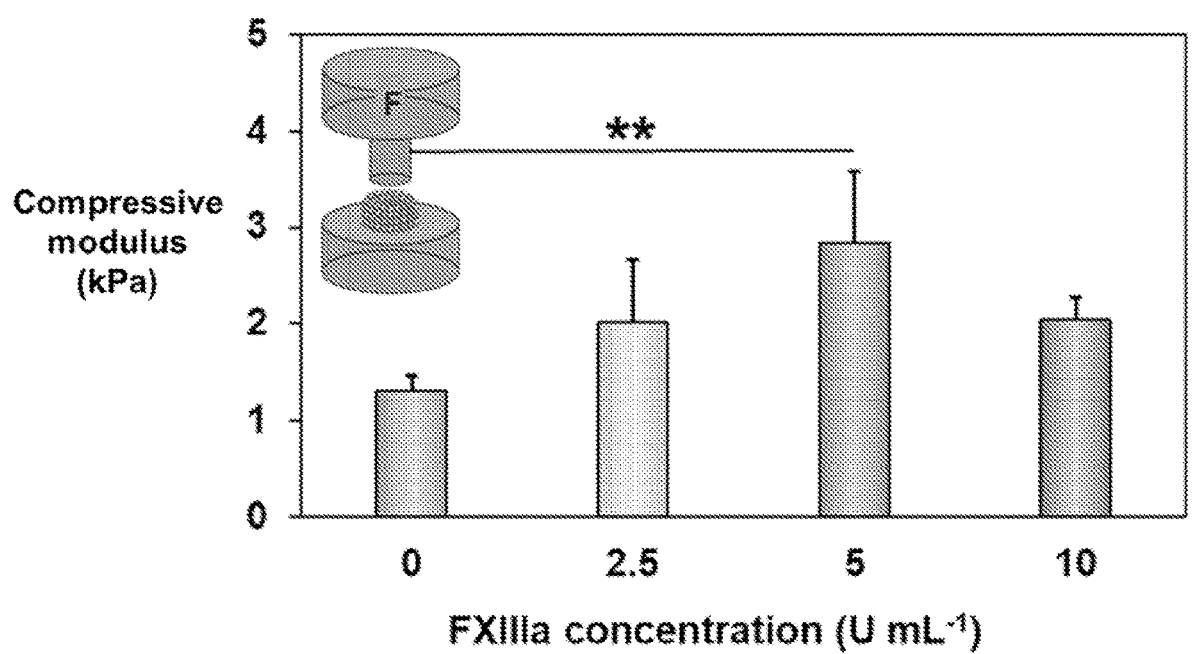
FIG. 4D shows compressive modulus of gelatin methacryloyl granular hydrogel scaffolds assembled via reacting medium gelatin methacryloyl hydrogel microparticles with activated factor XIII (concentrations of 0, 2.5, 5, or 10 U mL$^{-1}$) for 1.5 h. The data represents mean # standard deviation for at least 3 samples.

FIG. 4D shows the compressive modulus of unassembled (FXIIIa concentration=0) and assembled GHS with the FXIIIa concentration of 2.5, 5, and 10 U mL$^{-1}$. The average compressive modulus of unassembled GHS (i.e., packed HMP) was around 1.31±0.15 kPa, and that of assembled GHS was 2.02±0.64, 2.83±0.74, and 2.05±0.22 kPa for the FXIIIa concentrations of 2.5, 5, and 10 U mL$^{-1}$, respectively. Accordingly, FXIIIa with a concentration of 5 U mL$^{-1}$, obtained from activating FXIII using thrombin (1 U mL$^{-1}$), resulted in GHS stiffness that was significantly higher than the control group (no FXIII), which will be used as the optimum enzyme concentrations for the GHS formation (see FIG. 4D).

Figure 4E:
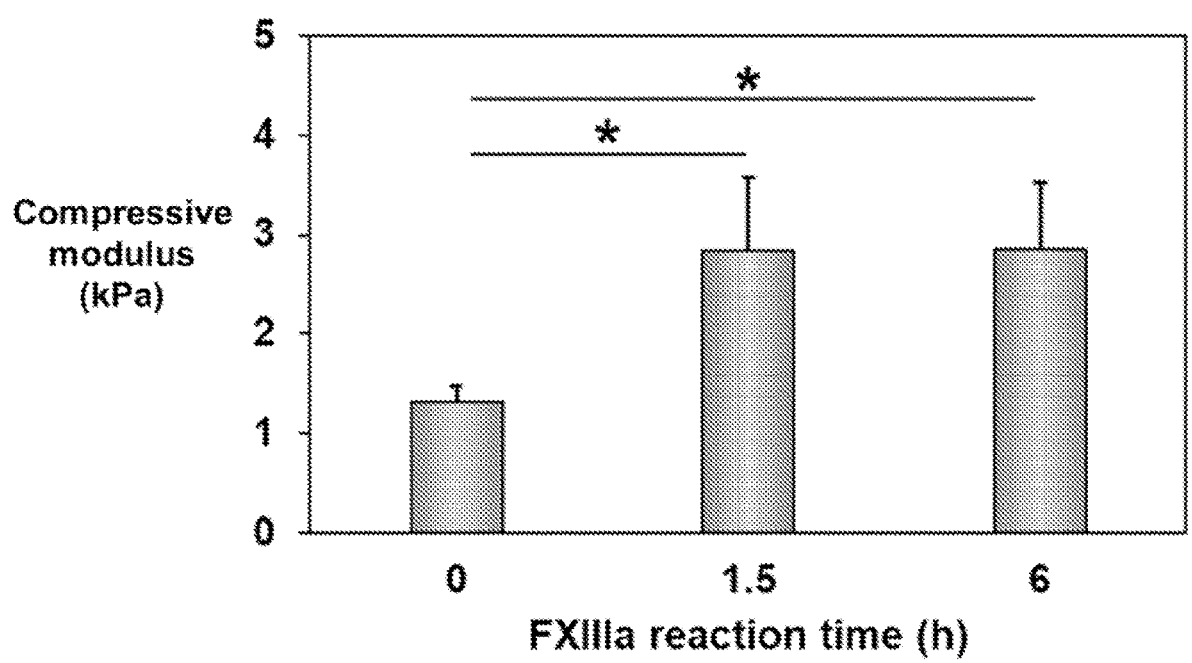
FIG. 4E shows the effect of activated factor XIII (5 U mL$^{-1}$) reaction time at 37° C. on the compressive modulus of gelatin methacryloyl granular hydrogel scaffolds. The data represents mean±standard deviation for at least 3 samples.

FIG. 4E shows the compressive modulus of GelMA GHS formed at two different FXIIIa reaction times (1.5 and 6 h) compared with the packed HMP that did not undergo the FXIIIa reaction. The compressive modulus of assembled GHS at the FXIIIa concentration of 5 U mL$^{-1}$ was around 2.83±0.74 or 2.36±0.96 kPa for the GHS incubation time of 1.5 or 6 h at 37° C., respectively. These results show that the scaffold stiffness reaches a plateau after 1.5 h of incubation at 37° C. Therefore, the scaffolds are less likely to undergo further stiffening after 1.5 h post injection in tissues, such as brain.

Figure 5A:
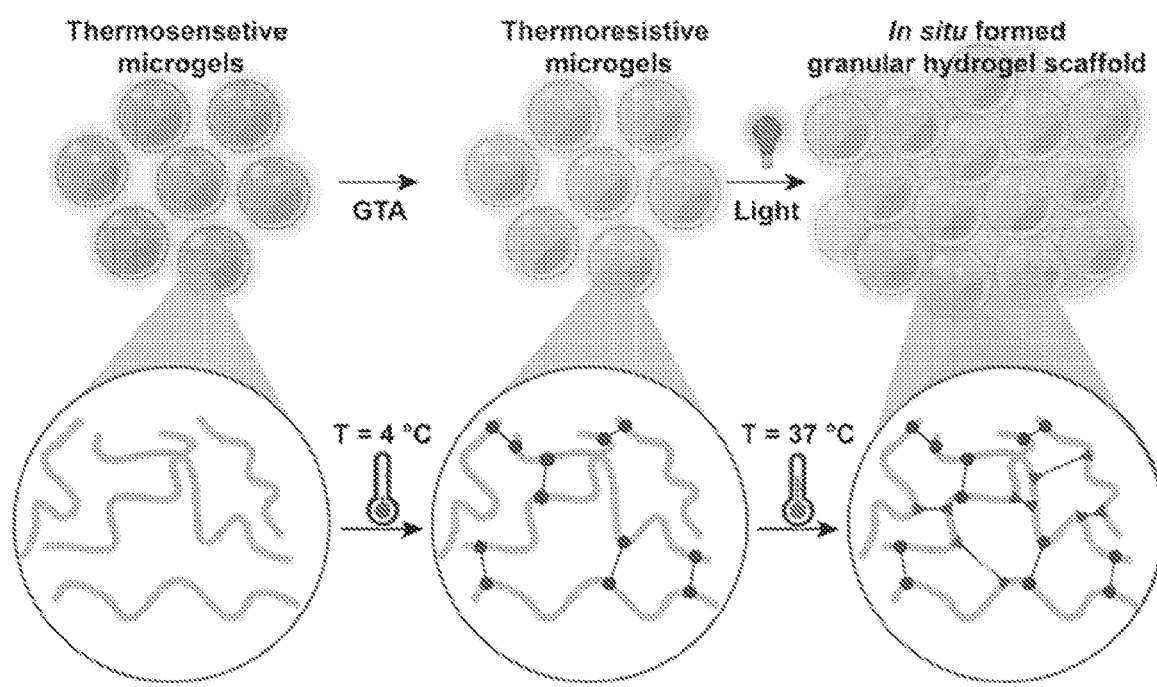
FIGS. 5A-C show in situ fabrication of granular hydrogel scaffolds from thermoresistive GelMA microgels (scale bar is 200 μm).
Figure 5B:
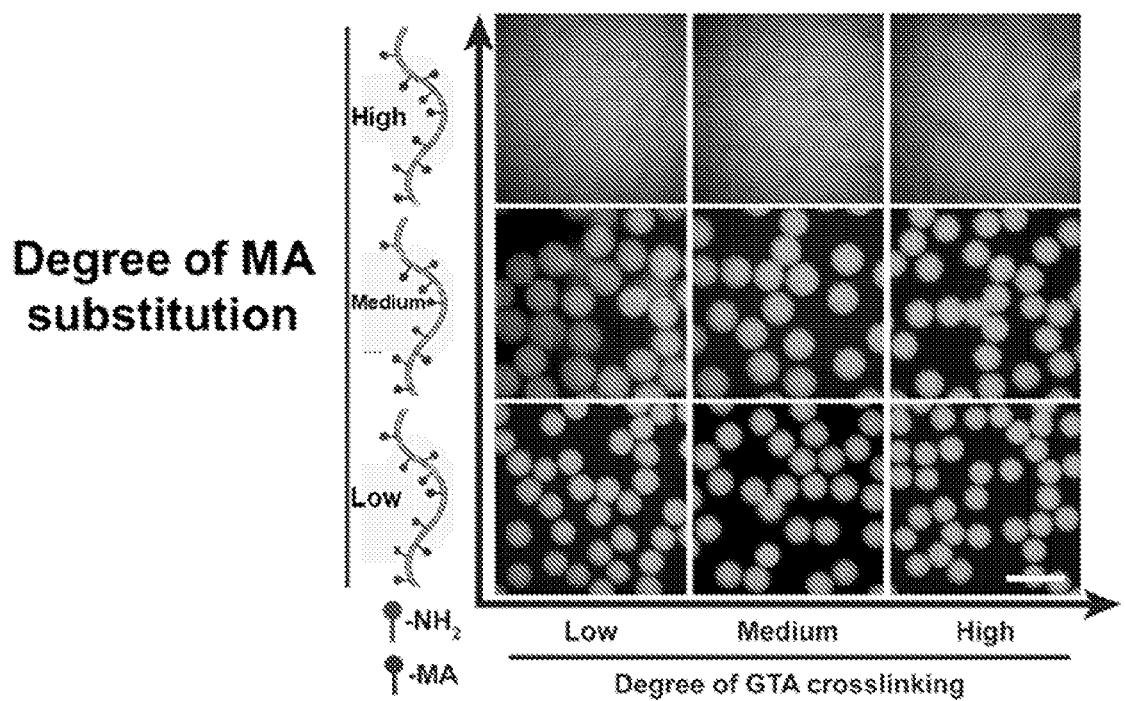
Figure 5C:
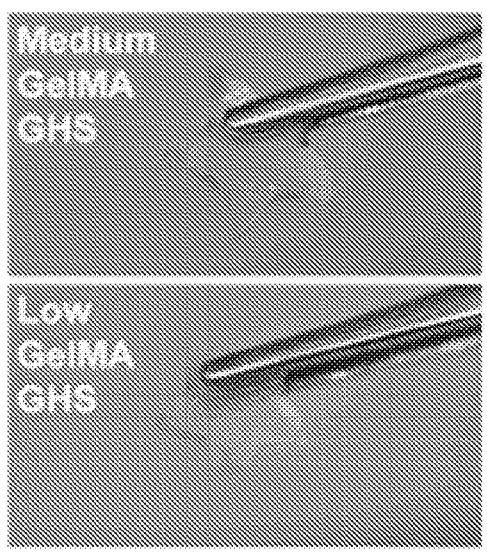

FIGS. 5A-C show in situ formation of GHS from thermoresistive GelMA microgels. FIG. 5A shows that GelMA HMP are thermoresponsive and unable to form a scaffold at body temperature (e.g., 37° C.). To overcome this limitation, the GelMA HMP was crosslinked via a Schiff-base reaction to produce thermoresistant microgels. These thermoresistive microgels served as building blocks for the in situ fabrication of GHS via radical photopolymerization.

FIG. 5B shows that GelMA was synthesized using three different degrees of substitutions (DOS) with high (~70%), medium (~40%) and low (~10%), which affected the availability of primary amine groups for Schiff-base crosslinking using glutaraldehyde (GTA). High DoS resulted in insufficient primary amine groups, making the thermoresistive microgel unstable. In contrast, medium and low DoS resulted in stable thermoresistive microgels.

FIG. 5C shows thermoresistive microgels from medium and low GelMA were scaffolded to form a mechanically stable GHS.

Figure 6A:
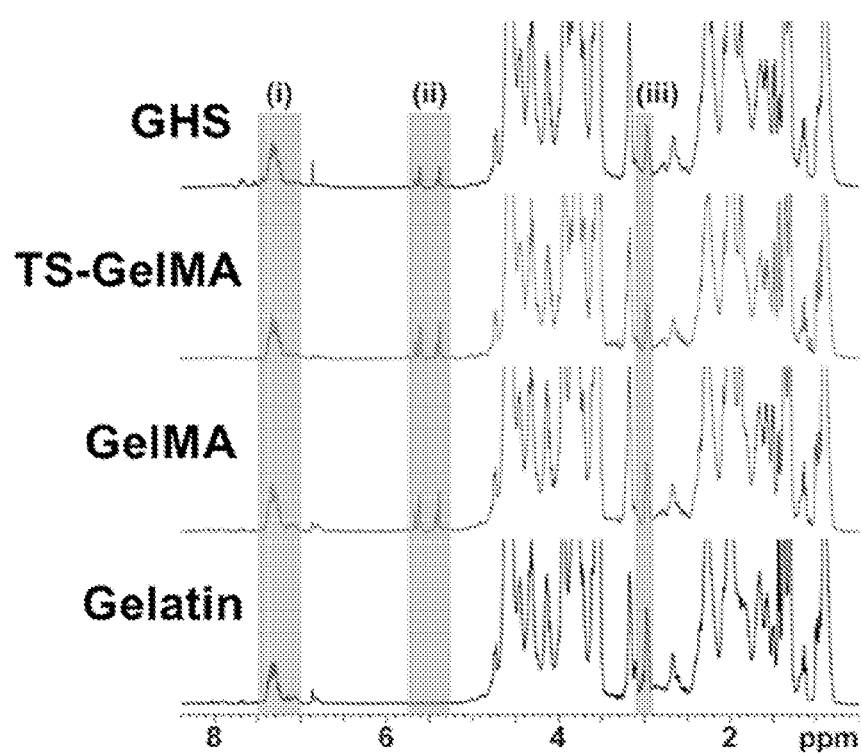
FIGS. 6A-D show material and mechanical characterization of granular hydrogel scaffolds made from thermoresistive GelMA microgels.

FIGS. 6A-D show material and mechanical characterization of GHS made from thermoresistant microgels. FIG. 6A shows $^1$H NMR spectrometry of pure gelatin microgel, uncrosslinked GelMA microgel (with medium DoS), thermoresistant GelMA HMP, and photocrosslinked GHS composed of thermoresistant microgels. The peaks for aromatic acids (i) serve as the reference in all the groups. The presence of vinyl groups (ii) and a decrease in lysine protons (iii) were also observed.

Figure 6B:
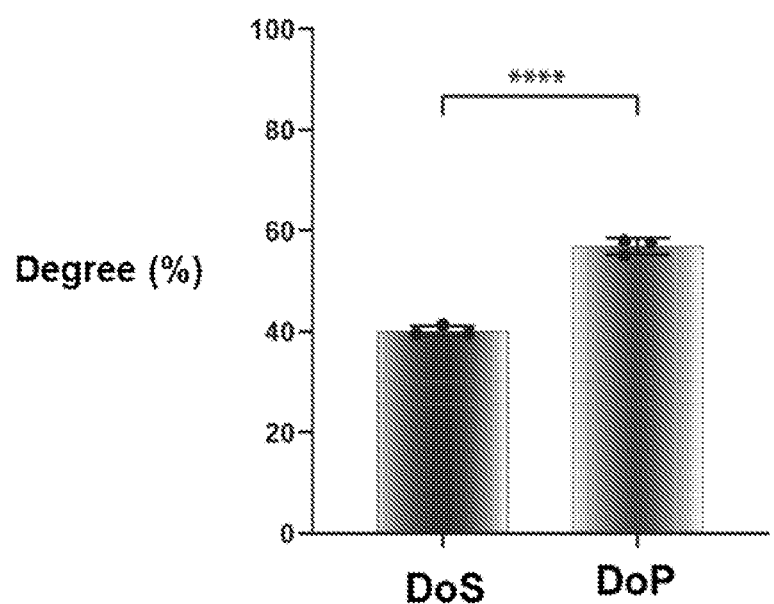

FIG. 6B shows oscillatory strain sweep at constant frequency of 1 rad/s performed on in situ fabricated scaffolds: GHS from thermoresistant GelMA microgels (TS GelMA GHS), GHS from thermoresponsive GelMA microgels (GelMA GHS), and conventional (bulk) GelMA scaffolds.

Figure 6C:
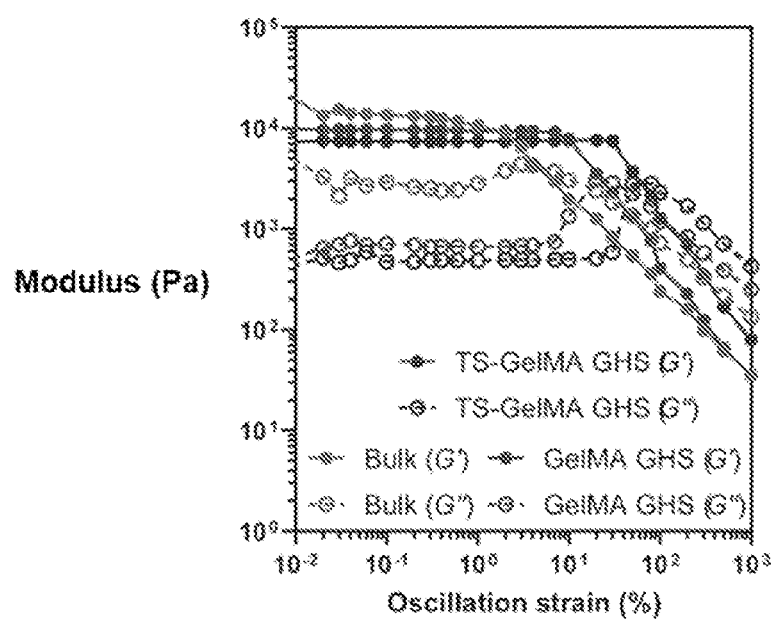

FIG. 6C shows dynamic moduli versus oscillation strain for different scaffolds at a constant frequency of 1 rad/s, showing the storage and loss moduli of TS GelMA GHS, GelMA GHS, and conventional (bulk) GelMA scaffolds.

Figure 6D:
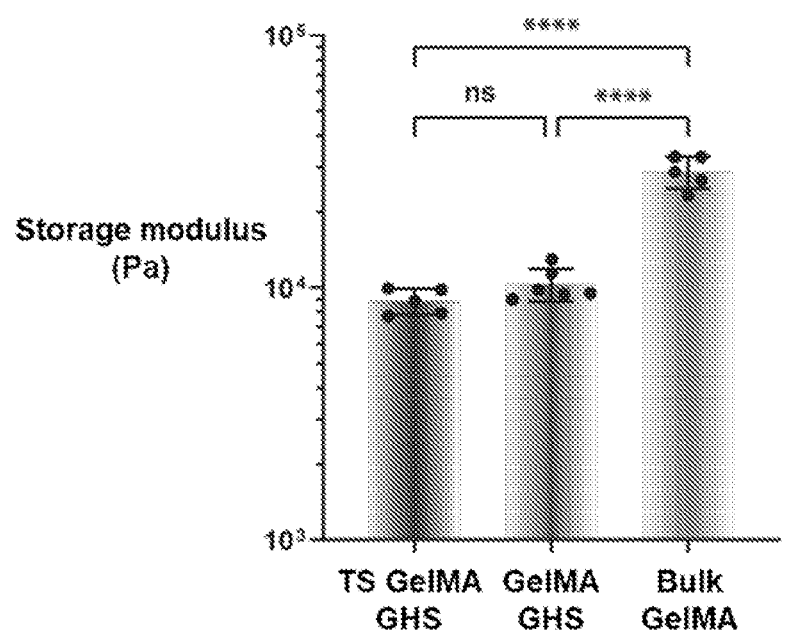

FIG. 6D shows the storage modulus measured at 1 rad/s and 0.1% strain. No significant difference was observed between the TS GelMA GHS and GelMA GHS, but bulk GelMA had significantly higher stiffness.

Figure 7A:
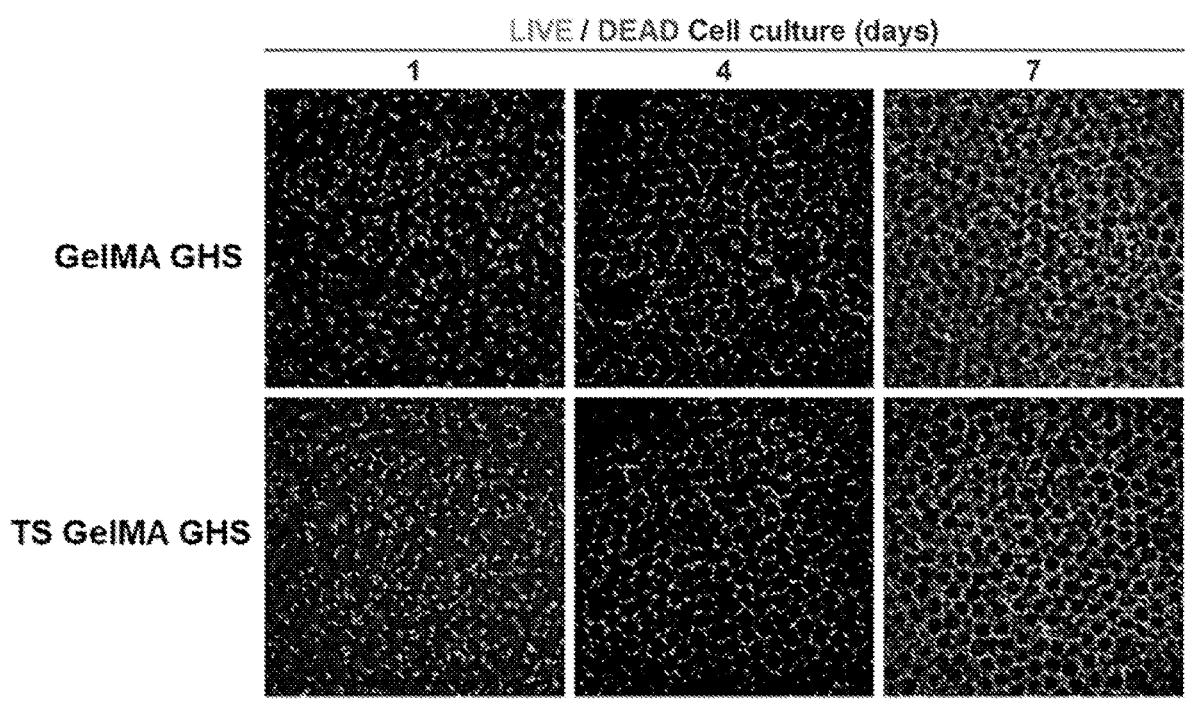
FIGS. 7A-C show biocompatibility assessment of granular hydrogel scaffolds made from thermoresistive GelMA microgels.
Figure 7B:
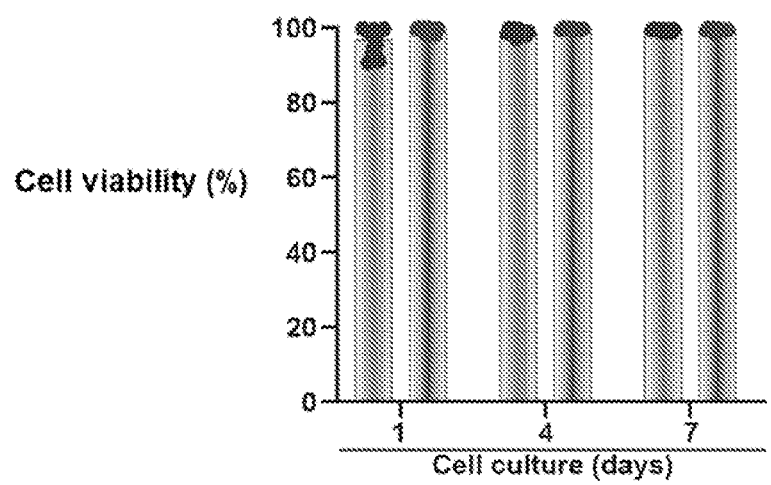
Figure 7C:
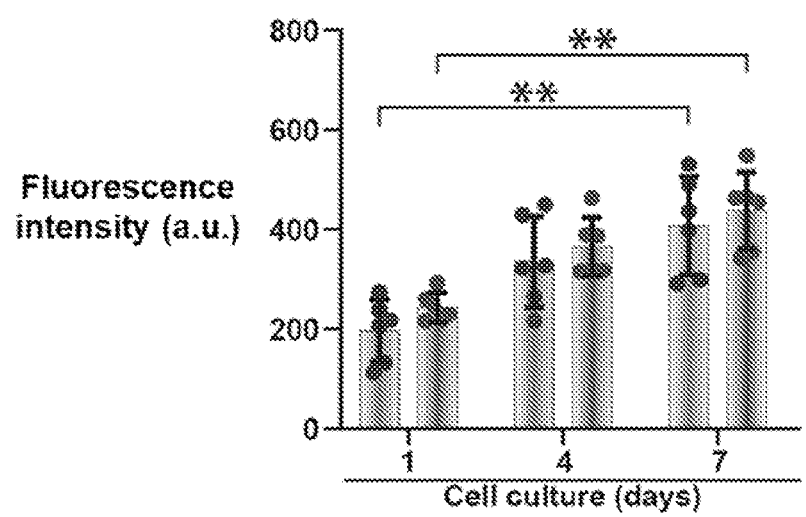

FIGS. 7A-C show biocompatibility assessment of GHS made from thermoresistant microgels. FIG. 7A shows that NIH-3T3 murine fibroblast cells were mixed with thermoresponsive or thermoresistant microgels, then photocrosslinked to form GelMA GHS or TS GelMA GHS, respectively. Fluorescent microscopy using a combination of green (representing live cells) and red (representing dead cells) dyes was performed over a period of 7 days, demonstrating cell proliferation and viability.

FIG. 7B shows the results if cell viability percentage indicated a consistently high viability rate (~100%) for all GHS samples.

REFERENCES

Each of the following references is incorporated herein by reference in its entirety.

[1] Nichol, J. W.; Koshy, S. T.; Bae, H.; Hwang, C. M.; Yamanlar, S.; Khademhosseini, A. Cell-Laden Microengineered Gelatin Methacrylate Hydrogels. *Biomaterials* 2010, 31 (21), 5536-5544. https://doi.org/10.1016/J.BIOMATERIALS.2010.03.064.

[2] Yue, K.; Trujillo-de Santiago, G.; Alvarez, M. M.; Tamayol, A.; Annabi, N.; Khademhosseini, A. Synthesis, Properties, and Biomedical Applications of Gelatin Methacryloyl (GelMA) Hydrogels. *Biomaterials* 2015, 73, 254-271. https://doi.org/10.1016/J.BIOMATERIALS.2015.08.045.

[3] Sheikhi, A.; de Rutte, J.; Haghniaz, R.; Akouissi, O.; Sohrabi, A.; di Carlo, D.; Khademhosseini, A. Microfluidic-Enabled Bottom-up Hydrogels from Annealable Naturally-Derived Protein Microbeads. *Biomaterials* 2019, 192, 560-568. https://doi.org/10.1016/J.BIOMATERIALS.2018.10.040.

[4] Sheikhi, A.; de Rutte, J.; Haghniaz, R.; Akouissi, O.; Sohrabi, A.; di Carlo, D.; Khademhosseini, A. Modular Microporous Hydrogels Formed from Microgel Beads with Orthogonal Thermo-Chemical Responsivity: Microfluidic Fabrication and Characterization. *Methods X* 2019, 6, 1747-1752. https://doi.org/10.1016/J.MEX.2019.07.018.

[5] de Rutte, J. M.; Koh, J.; di Carlo, D. Scalable High-Throughput Production of Modular Microgels for In Situ Assembly of Microporous Tissue Scaffolds. *Advanced Functional Materials* 2019, 29 (25), 1900071. https://doi.org/10.1002/ADFM.201900071.

[6] Griffin, D. R.; Weaver, W. M.; Scumpia, P. O.; di Carlo, D.; Segura, T. Accelerated Wound Healing by Injectable Microporous Gel Scaffolds Assembled from Annealed Building Blocks. *Nature Materials* 2015, 14(7), 737-744. https://doi.org/10.1038/NMAT4294.

[7] Koshy, S. T.; Desai, R. M.; Joly, P.; Li, J.; Bagrodia, R. K.; Lewin, S. A.; Joshi, N. S.; Mooney, D. J. Click-Crosslinked Injectable Gelatin Hydrogels. *Advanced Healthcare Materials* 2016, 5 (5), 541-547. https://doi.org/10.1002/ADHM.201500757.

[8] Zoratto, N.; di Lisa, D.; de Rutte, J.; Sakib, M. N.; Alves e Silva, A. R.; Tamayol, A.; di Carlo, D.; Khademhosseini, A.; Sheikhi, A. In Situ Forming Microporous Gelatin Methacryloyl Hydrogel Scaffolds from Thermostable Microgels for Tissue Engineering. *Bioengineering & Translational Medicine* 2020, 5 (3), e10180. https://doi.org/10.1002/BTM2.10180.

[9] Nih, L. R.; Gojgini, S.; Carmichael, S. T.; Segura, T. Dual-Function Injectable Angiogenic Biomaterial for the Repair of Brain Tissue Following Stroke. *Nature Materials* 2018 17:7 2018, 17 (7), 642-651. https://doi.org/10.1038/s41563-018-0083-8.

[10] Ali, M.; Su, S.; Filipe, C. D. M.; Pelton, R.; Li, Y. Enzymatic Manipulations of DNA Oligonucleotides on Microgel: Towards Development of DNA-Microgel Bioassays{. https://doi.org/10.1039/b709817k.

[11] Nih, L. R.; Sideris, E.; Thomas Carmichael, S.; Segura, T.; Nih, L. R.; Sideris, E.; Segura, T.; Carmichael, S. T. Injection of Microporous Annealing Particle (MAP) Hydrogels in the Stroke Cavity Reduces Gliosis and Inflammation and Promotes NPC Migration to the Lesion. *Advanced Materials* 2017, 29 (32), 1606471. https://doi.org/10.1002/ADMA.201606471.

[12] Zoratto, N.; di Lisa, D.; de Rutte, J.; Sakib, M. N.; Alves e Silva, A. R.; Tamayol, A.; di Carlo, D.; Khademhosseini, A.; Sheikhi, A. In Situ Forming Microporous Gelatin Methacryloyl Hydrogel Scaffolds from Thermostable Microgels for Tissue Engineering. *Bioengineering & Translational Medicine* 2020, 5 (3), e10180. https://doi.org/10.1002/BTM2.10180.

[13] Zaman Ataei; Sina Kheirabadi; Jenna Zhang; Alexander Kedzierski; Carter Petrosky; Rhea Jiang; Christian Vollberg. Nanoengineered Granular Hydrogel Bioinks with Preserved Interconnected Microporosity for Extrusion Bioprinting. *Small* 2022, No. Accepted.

[14] Yue, K.; Li, X.; Schrobback, K.; Sheikhi, A.; Annabi, N.; Leijten, J.; Zhang, W.; Zhang, Y. S.; Hutmacher, D. W.; Klein, T. J.; Khademhosseini, A. Structural Analysis of Photocrosslinkable Methacryloyl-Modified Protein Derivatives. *Biomaterials* 2017, 139, 163-171. https://doi.org/10.1016/J.BIOMATERIALS.2017.04.050.

[15] Kashiwagi, T.; Yokoyama, K. ichi; Ishikawa, K.; Ono, K.; Ejima, D.; Matsui, H.; Suzuki, E. ichiro. Crystal Structure of Microbial Transglutaminase From Streptoverticillium Mobaraense *.*Journal of Biological Chemistry* 2002, 277 (46), 44252-44260. https://doi.org/10.1074/JBC.M203933200.

[16] Georges, P. C.; Miller, W. J.; Meaney, D. F.; Sawyer, E. S.; Janmey, P. A. Matrices with Compliance Comparable to That of Brain Tissue Select Neuronal over Glial Growth in Mixed Cortical Cultures. *Biophysical Journal* 2006, 90 (8), 3012-3018. https://doi.org/10.1529/BIOPHYSJ.105.073114.

It should be understood that the disclosure of a range of values is a disclosure of every numerical value within that range, including the end points. It should also be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be apparent to those skilled in the art that numerous modifications and variations of the described examples and embodiments are possible considering the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

It should be understood that modifications to the embodiments disclosed herein can be made to meet a particular set of design criteria. Therefore, while certain exemplary embodiments of the apparatus and methods of using and making the same disclosed herein have been discussed and illustrated, it is to be distinctly understood that the invention is not limited thereto but may be otherwise variously embodied and practiced within the scope of the following claims.

What is claimed is:

1. A method of forming a granular hydrogel scaffold, the method comprising:
   converting polymers or lipids to form hydrogel microparticles via a first crosslinking;
   injecting the hydrogel microparticles into a tissue;
   assembling the hydrogel microparticles to form the granular hydrogel scaffold via a second crosslinking, wherein the second crosslinking is a non-light-mediated crosslinking; and
   mixing the hydrogel microparticles with additional polymers and/or colloidal particles prior to assembling the hydrogel microparticles, wherein the additional polymers are selected from the group consisting of aldehyde-modified carbohydrates, proteoglycans, and mixtures thereof.

2. The method of claim 1, wherein the polymers are selected from the group consisting of proteins, peptides, and carbohydrates.

3. The method of claim 1, wherein the first crosslinking comprises physical crosslinking and/or chemical crosslinking.

4. The method of claim 1, further comprising:
   decorating the hydrogel microparticles with biologics and/or colloidal particles and/or hybrid biologics-colloids prior to assembling the hydrogel microparticles or encapsulating biologics and/or colloidal particles and/or hybrid biologics-colloids in the hydrogel microparticles.

5. The method of claim 4, wherein decorating the hydrogel microparticles with the biologics and/or colloidal particles and/or hybrid biologics-colloids comprises coating the hydrogel microparticles with biologics and/or colloidal particles and/or hybrid biologics-colloids.

6. The method of claim 1, further comprising:
   encapsulating or loading biologics and/or colloidal particles and/or hybrid biologics-colloids in the hydrogel microparticles prior to assembling the hydrogel microparticles.

7. The method of claim 4, wherein the biologics and/or colloidal particles and/or hybrid biologics-colloids that decorate the hydrogel microparticles are loaded to, attached on the surface of, or hybridized with nanocarriers bearing crosslinkable functional groups.

8. The method of claim 4, wherein the biologics are selected from the group consisting of biomolecules, growth factors, cytokines, enzymatically modified DNA, drugs, and peptides.

9. The method of claim 4, wherein the biologics are physically and/or chemically attached to the colloidal particles and/or the hybrid biologics-colloids that decorate the hydrogel microparticles.

10. The method of claim 9, wherein the colloidal particles which are mixed with the hydrogel microparticles prior to assembling the hydrogel microparticles, or which decorate the hydrogel microparticles, are heparin nanoparticles.

11. The method of claim 8, wherein the biologics comprise growth factors, and wherein the growth factors are physically and/or chemically attached to the colloidal particles and/or the hybrid biologics-colloids which decorate the hydrogel microparticles.

12. The method of claim 11, wherein the colloidal particles which are mixed with the hydrogel microparticles prior to assembling the hydrogel microparticles, or which decorate the hydrogel microparticles, are heparin nanoparticles.

* * * * *